(12) United States Patent
Fisher

(10) Patent No.: US 7,803,352 B2
(45) Date of Patent: Sep. 28, 2010

(54) METHOD FOR CONTINUOUS VISUALIZATION OF A BLOOD CLOT OR PLAQUE IN BODY LUMEN

(76) Inventor: John Steele Fisher, 310 Palmetto Rd., Belleair, FL (US) 33756

( * ) Notice: Subject to any disclaimer, the term of this patent is extended or adjusted under 35 U.S.C. 154(b) by 1356 days.

(21) Appl. No.: 10/982,990

(22) Filed: Nov. 5, 2004

(65) Prior Publication Data

US 2005/0063904 A1    Mar. 24, 2005

Related U.S. Application Data

(63) Continuation-in-part of application No. 10/383,796, filed on Mar. 7, 2003, now abandoned.

(51) Int. Cl.
*A61B 5/055* (2006.01)

(52) U.S. Cl. ............... 424/9.3; 424/1.11; 424/1.65; 424/9.1; 424/9.4; 424/9.6

(58) Field of Classification Search ............... 424/1.11, 424/1.37, 1.65, 1.41, 1.49, 9.1, 9.3, 9.4, 9.5, 424/9.6, 9.7, 9.8, 9.34, 9.52, 1.69, 1.73, 1.81, 424/1.85, 1.89

See application file for complete search history.

(56) References Cited

U.S. PATENT DOCUMENTS

| | | | |
|---|---|---|---|
| 3,975,512 A | 8/1976 | Long | 424/5 |
| 4,647,447 A | 3/1987 | Gries et al. | 424/9.36 |
| 4,770,183 A | 9/1988 | Groman et al. | 424/9.32 |
| 4,863,715 A | 9/1989 | Jacobsen et al. | 424/9.32 |
| 5,228,446 A | 7/1993 | Unger et al. | 424/9.51 |
| 5,364,613 A | 11/1994 | Sieving et al. | 424/9.3 |
| 5,387,080 A | 2/1995 | Bouhennicha et al. | 415/150 |
| 5,447,711 A | 9/1995 | Almen et al. | 424/9.452 |
| 5,978,698 A | 11/1999 | Sax | 600/431 |
| 6,051,207 A | 4/2000 | Klaveness et al. | 424/9.1 |
| 6,139,819 A | 10/2000 | Unger et al. | 424/9.52 |
| 6,149,891 A | 11/2000 | Korenstein et al. | 424/9.4 |
| 6,192,264 B1 | 2/2001 | Foo et al. | 600/413 |
| 6,265,875 B1 | 7/2001 | Saranathan | 324/314 |
| 6,303,101 B1 | 10/2001 | Klaveness et al. | 424/9.1 |
| 6,310,243 B1 | 10/2001 | Almen et al. | 564/153 |
| 6,404,680 B1 | 6/2002 | Kwon | 424/9.4 |
| 6,406,680 B1 | 6/2002 | Priebe | 424/9.4 |
| 6,420,436 B1 | 7/2002 | Kirkland | 514/772 |
| 6,448,442 B1 | 9/2002 | Almen et al. | 564/153 |
| 6,869,590 B2 * | 3/2005 | Edwards et al. | 424/1.65 |

FOREIGN PATENT DOCUMENTS

| | | |
|---|---|---|
| WO | WO98/57578 | 12/1998 |
| WO | WO01/09188 | 2/2001 |
| WO | WO01/91805 | 12/2001 |
| WO | WO02/02173 | 1/2002 |
| WO | WO2004/017907 | 3/2004 |

OTHER PUBLICATIONS

Kalki et al, J. Nucl. Med., 1997, vol. 38, No. 10, pp. 1535-1540.*
European Supplementary Partial Search Report dated May 18, 2006 in regards to European Patent Application No. 04717983.3.
Van Lysel, Michael S. "X-Ray Projection Angiography". Biomedical Engineering Handbook. 2000, pp. 61-68.
Stuber et al. "Selective Three-Dimensional Visualization of the Coronary Arterial Lumen Using Arterial Spin Tagging". Magnetic Resonance in Medicine. Feb. 2002, vol. 47, No. 2, pp. 322-329.
Wacker et al. "MR Image-Guided Endovascular Procedures With the Ultrasmall Superparamagnetic iron oxide SH U 555 C as an Intravascular Contrast Agent: Study in Pigs". Radiology. Feb. 2003, vol. 226, No. 2, pp. 459-464.
European Supplementary Search Report dated Feb. 28, 2008 based on EP application No. EP05757188.
Butler et al. "*Rapid localization of indium-111-labeled inhibited recombinant tissue plasminogen activator in a rabbit thrombosis model*," Journal of Nuclear Medicine; vol. 32, Issue 3, Mar. 1, 1991 (abstract only).
De Bruyn et al. "*Visualization of Thrombi in Pulmonary Arteries With Radiolabeled, Enzymatically Inactivated Tissue-type Plasminogen Activator*," Circulation, 1995, 92, pp. 1320-1325.
Butler et al. "*Detection of Postoperative Deep-Venous Thrombosis Using Technetium-99m-Labeled Tissue Plasminogen Activator*," Journal of Nuclear Medicine; vol. 38, No. 2, Feb. 1997, pp. 219-223.
Butler et al. "*Technetium-99m-Modified Recombinant Tissue Plasminogen Activator to Detect Deep Venous Thrombosis*," The Journal of Nuclean Medicine, vol. 37, No. 5, May 1996. pp. 744-748.

* cited by examiner

*Primary Examiner*—D L Jones
(74) *Attorney, Agent, or Firm*—Ohlandt, Greeley, Ruggiero & Perle, LLP

(57) ABSTRACT

A method for visualizing a blood clot or plaque disposed within a body lumen comprising: binding a contrasting complex comprising a contrast material and a thrombolytic material or a clot dissolving agent to the blood clot or plaque; and visualizing the blood clot or plaque over a period time by a visualizing system.

9 Claims, No Drawings

METHOD FOR CONTINUOUS VISUALIZATION OF A BLOOD CLOT OR PLAQUE IN BODY LUMEN

This application is a continuation-in-part application of U.S. patent application Ser. No. 10/383,796, filed on Mar. 7, 2003 now abandoned.

BACKGROUND OF THE INVENTION

1. Field of the Invention

The present invention relates to diagnostic imaging contrast compositions and method of using such compositions. More particularly, the present invention relates to imaging blood clots or plaque disposed within a body lumen, especially those of the circulatory system, and provide extended visualization for invasive medical diagnostic and therapeutic procedures.

2. Description of the Prior Art

Contrast materials have long been used in a variety of medical imaging procedures to enhance the contrast of patient images. Contrast materials or media containing contrast materials may, for example, be employed with x-ray, magnetic resonance and ultrasound imaging. Such imaging procedures involve visualization of lumens, such as blood vessels in cardiac angiography, either by x-ray imaging or by magnetic resonance imaging (MRI), intravenous urography or kidney imaging, computerized tomography, neurological visualization of the central nervous system (i.e., the spinal cord, brain etc.), the digestive tract, lymphatics, bronchi, biliary ducts and the like. Imaging procedures are widely used in the practice of contemporary medicine. There are more than 10 million x-ray radiological examinations involving the use of contrast media performed each year in the United States and the number is growing. It is estimated that approximately 5-10% of these procedures are accompanied by clinical side effects with life threatening complications occurring in a portion of such procedures. The use of any particular contrast medium is related to its diagnostic efficacy, its toxicity, its ease of storage and administration, and by consideration of adverse effects it may have on the patient to which it is administered. It is desirable to have contrast media that are effective and have as few as possible deleterious physiological effects on body cells or organs.

In medical procedures involving the use of contrast media, there are several undesirable side effects including hyperosmotic damage, iodine-specific toxicity, kidney damage, and radiation damage. As an example, it is typical to inject 100-200 mL of contrast medium into a total plasma volume of 5 liters within a period of several minutes. Cells, such as endothelial cells, red blood cells, white blood cells, kidney cell etc., are exposed to a hyperosmotic solution in comparison to the osmolarity of the blood. This gives rise to hyperosmotic shock which may produce damage. This hypertonicity causes osmotic effects, such as the draining of water from red blood cells, endothelia cells, and heart and blood vessel muscle cells. Hypertonicity, chemotoxicity, and non-optimal ionic composition either individually or collectively reduce the contractile force of the muscle cells and cause dilation of small blood vessels and result in a decrease in blood pressure.

Iodine is commonly used in contrast media. For example, in an x-ray visualization procedure typically 30-40 grams of iodine/contrast medium are injected into the blood within a period of about 2-10 minutes. Visualization of a target requires a minimum accumulation of 15-20 mg of iodine/ml in the target tissue. For this reason, the initial iodine concentration of the contrast medium is relatively high (i.e., in the range of about 300 to 420 mg iodine/ml of medium). Iodinated aromatic compounds may be used as x-ray contrast materials. U.S. Pat. No. 6,406,680 is directed to iodinated alkenes for use as x-ray contrast materials reported as equivalent to iodinated aromatic contrast materials. Compounds that can release iodide in reactions with nucleophiles or electrophiles may cause toxic biological effects and preferably should not be used as contrast materials.

As iodine is a common contrast material, the iodine load to which the kidney is exposed and needs to excrete is a potential cause for renal damage. In general, it is believed that about 12% of all patients that are injected with an x-ray contrast medium encounter renal complications. In cardiac catheterization, for example, from 9-16% of patients develop renal failure depending upon whether they are high or low risk patients. It is well known that exposure of cells to x-ray contrast medium causes cell damage. In addition, with commercial x-ray contrast media having high concentrations of iodine of about 300 mg iodine/mL, these media have a relatively high viscosity at ambient temperature. Such high viscosity is troublesome to the provider of the contrast medium and requires relatively large bore needles or high-applied pressure. This is particularly significant in pediatric radiography and in radiographic techniques, such as angiography, which require rapid bolus administration. Although the toxicity of iodine as a contrast material is notable, toxicity and adverse biological effects of a contrast medium are attributed to the components of a the medium, such as the solvent or carrier, as well as the contrast material itself and its components (i.e., ions if ionic) and various metabolites.

Coronary angiography is an important procedure in the diagnosis of medical problems associated with the coronary arteries that supply blood to the heart. During this procedure, the coronary arteries are imaged so as to enable the medical practitioner to observe any blood circulation problems that may affect the heart. A radio-opaque contrast substance (i.e., contrast medium with iodine as the active contrast material) injected into the coronary arteries during the angiography procedure causes the arteries to appear as bright lines contrasted against a relatively darker background. Where a stenosis or restriction is present in a coronary artery, the artery will appear to be pinched and will have a smaller cross-sectional thickness at the location of the restriction. It is typically necessary to produce at least five angiography sequences at different projection angles relative to the heart to obtain visual images of all portions of the coronary arterial system for accurate medical diagnosis.

During angiography, a radio-opaque contrast substance is injected into one of the coronary arteries and consecutive frames (i.e., from about 150 to 250) are recorded on film with a cine camera, video camera, and/or recorded in digital format. Multiple injections or sequences are usually involved with an angiography procedure. Each sequence records from 5 to 15 heartbeats or cardiac cycles. During each beat of the heart, ventricles fill with blood during diastole and reach their maximum volume at the end of diastole. The heart muscle then contracts during the systole phase, and the ventricles reach their minimum volume of blood at the end of systole. The filling of the coronary arteries with blood takes place primarily during diastole as the coronary arteries pass through the heart muscle and the pressure exerted by the contracting muscle during the systole phase tends to impede blood flow through the arteries. During the imaging procedure, the injected radio-opaque contrast substance can be seen to fill the coronary artery and then to gradually clear from the artery as fresh blood devoid of the contrast substance enters the artery.

Contrast media used in coronary angiography are injected into the circulatory system and have been associated with several serious adverse effects on cardiac function. In this procedure following injection of the contrast medium, a bolus of the contrast medium rather than blood flows through the circulatory system. Differences in the chemical and physical nature of the contrast medium and the blood that it displaces temporarily may produce undesirable side effects, such as arrhythmias, reduction in cardiac contractile force, ventricular fibrillation and the like. Accordingly, it is a desirable objective to reduce such negative effects on cardiac function from the infusion of contrast media into the circulatory system during angiography and other similar procedures. In MRI methodology for visualization of blood vessels, a paramagnetic substance dissolved in a hyperosmotic contrast medium is injected. Factors contributing to contrast media toxicity are chemotoxicity of the contrast material, osmolalilty of the contrast medium, and the ionic/non-ionic composition of the contrast medium.

Coronary artery disease is currently the leading cause of death in the Western Hemisphere. Accordingly, visualization of the coronary arteries is a critical step in the diagnosis, treatment and prevention of death and disability from this disease. While angiography, the mapping of blood vessels, is performed with a number of techniques, the most commonly employed procedures involve invasive techniques (i.e., x-ray angiography, nuclear medicine, or surgery). Angiography commonly involves the injection for contrast of an x-ray opaque dye into the patient, allowing a period of time to pass in order to permit the dye to become circulated within the blood stream, and thereafter exposing the patient to ionizing radiation (e.g., x-rays) in order to image the patient's blood vessels. In x-ray radiography, a catheter for injection of contrast material is inserted into the artery through the groin area of a patient. Passive non-invasive techniques such as magnetic resonance imaging may also be employed. U.S. Pat. No. 6,265,875 is directed to a method of MRI tissue differentiation.

The various visualization techniques each have their disadvantages. For example, x-ray techniques expose both the patient and provider to dangerous ionizing radiation in order to image blood vessels of the patient. While in general exposure to x-rays (i.e., ionizing radiation) is preferably avoided, it is particularly undesirable in certain circumstances (i.e., pregnancy). Angiography generally requires high contrast between tissue and blood vessels in a patient to visualize blood vessels. In MRI systems, the patient must remain still for an extended period of time and expensive equipment is required. There is need for a methodology which allows angiography and other lumen visualizations without some of the disadvantages of conventional systems.

Other adverse side effects are associated with the use of contrast media. For example, patients often experience discomfort. Such discomfort is very commonly in the form of a burning sensation, experienced when the contrast medium is injected and subsequent to the injection. The severity and duration of such discomfort increases as the amount of contrast medium injected is increased. Also, contrast media may adversely affect a patient's kidneys. The extent of the effect of the contrast media on the patient's kidneys will depend on the patient's renal health and the amount and type of contrast media used. Contrast media generally fall into two general categories: (i) ionic contrast media; and (ii) non-ionic contrast media. In these groups, the contrast material in a carrier fluid is either in ionic form or in molecular or particulate form. In general, it is advisable to minimize the amount of contrast media employed. The amount of contrast medium used should be the smallest or minimal amount needed to provide diagnostically useful images of targets.

U.S. Pat. No. 5,394,874 is directed to angiography using ultrasound. Pulse echo ultrasonic imaging technology is used for examining the internal structure and functioning of living organisms, including blood flow. In medical diagnoses of various conditions, it is useful to examine soft tissues and/or blood flow to show structural details of body organs and vessels in the organs. In the examination of internal body structures, ultrasonic images are formed by producing very short pulses of ultrasound using a transducer, sending the pulses through the body, and thereafter measuring the properties of the echoes (e.g., amplitude and phase) from targets at various depths within the body. Typically, the ultrasound beam is focused at various depths within the body in order to improve resolution or image quality. A transducer receives the echoes, typically the same transducer used for transmission, and processed to generate an image of the target. Measuring and imaging blood flow, or other fluid flow, in the human body is typically done using the well-established Doppler principle, where a transmitted burst of ultrasound at a specific frequency is reflected from moving blood cells, thereby changing the frequency of the reflected ultrasound in accordance with the velocity and direction of the flow.

Regardless of the radiological imaging system (i.e., magnetic resonance imaging, computed tomography, or conventional radiograpahy using x-ray) or the part of the body being imaged, contrast-enhancing compositions are quite useful and widely employed by medical professionals. The use of contrast materials as adjuncts in radiological imaging makes it possible to determine the location, size, and conformation of organs or other structures of the body relative to surrounding tissues or structures. The various imaging systems, including radiological and sound systems, operate on distinct physical principles, and each may be used to differentiate between normal tissue, tumors, lesions, blockages and the like, but all may employ contrast materials. For example, in the diagnosis of disorders of the gastrointestinal (GI) tract, it is difficult to identify blockages or abnormalities in the conformation of the intestine unless the particular section of the GI tract under investigation is filled with a contrast material which facilitates definition of volumes and delineation of boundaries.

In conventional radiography, a beam of x-rays passes through a target and exposes an underlying photographic film thereby providing a visual image. The developed film gives an image of the radiodensity pattern of the target object. Less radio-dense areas show a blackening of the film and more radio-dense area (i.e., bone) produce a lighter image. Contrast materials for use with x-ray radiography may be either less or more radiodense than body tissues. Examples of less radio-dense contrast materials include air or other gases (i.e., carbon dioxide for use in the GI tract). Examples of more radio-dense contrast material included iodine compositions, barium sulfate suspensions, clay-based compositions, and the like. U.S. Pat. No. 3,975,512 is directed to the use of fluorocarbons as contrast enhancement media in radiological imaging. Depending on the imaging requirement, contrast materials are introduced into the body in various ways (i.e., orally with the GI tract; injection with coronary angiography). Regardless of the imaging system, a suitable contrast material must be biocompatible. Contrast materials should be non-toxic, chemically stable, should not be absorbed by the body or reactive within tissue, and should be safely eliminated from the body within a short period of time.

With reference to magnetic resonance imaging (MRI), a different physical principle is employed. MRI takes advantage of the fact that some atomic nuclei (e.g., hydrogen nuclei) have both nuclear spin and nuclear magnetic moment can therefore be manipulated by applied magnetic field. In conventional MRI systems, a magnetic field is established across a body to align the spin axes of the nuclei of a particular chemical element, usually hydrogen, with the direction of the magnetic field. The aligned spinning nuclei execute motions around the aligning direction of the magnetic field. The frequency at which the aligned spinning nuclei process around the direction of the magnetic field is a function of the particular nucleus which is involved and the strength of the magnetic field. In commercial MRI systems following alignment or polarization of the selected nuclei, a burst of radio frequency energy at the resonant frequency is radiated at the target object to produce a coherent deflection of the spin alignment of the selected nuclei. When the deflecting radio energy is terminated, the deflected or disturbed spin axes are reoriented or realigned and radiate a characteristic radio frequency signal which can be detected and analyzed. The MRI system can establish image contrast between different types of tissues in the body. A wide variety of different excitation and discrimination modes are known in the art. Accordingly, contrast materials for MRI must possess a substantially different concentration of the nuclei used as a basis for scanning. In a hydrogen scanning system, an imaging agent substantially lacking hydrogen can be used. In a MRI system scanning for a physiologically minor nucleus, e.g., fluorine nuclei, an imaging substance with a high concentration of hydrogen would provide appropriate contrast.

While MRI utilizes radio frequency pulses and magnetic field gradients applied to a patient in a strong field to produce visual images, contrast materials are used to improve magnetic resonance images. Such contrast materials include magnetizable substances having metals or metallic compounds. Such contrast materials may be paramagnetic, ferromagnetic, or supermagnetic and act through dipole interactions with tissue protons. Most magnetic resonance imaging contrast materials have similar mechanisms of action. Most are based on gadolinium chelates and are paramagnetic agents that develop a magnetic moment when placed in a magnetic. Magnetic resonance contrast materials are increasingly being used for magnetic resonance angiography. Both arterial and venous signals become equally enhanced. With current contrast materials, there is difficulty eliminating either arterial or venous signals for flow discrimination. Automatic bolus detection addresses this issue when the blood flow is in the arterial phase. However, with the contrast material in place, subsequent data must contend with the increased venous signal intensity as the contrast material continues to distribute in the system. In addition, it is expected that that the use of intravascular contrast materials with much longer persistence will require more novel techniques for arterial-venous discrimination. U.S. Pat. No. 6,192,264 is directed to a method for MRI venography including arterial and venous discrimination. Phase contrast magnetic resonance angiography is used for imaging blood flow.

Following heart disease and cancer, the most common cause of death in the United States is cerebrovascular disease. The most common cerebrovascular pathologies are: (i) stenoses or narrowing due to vessel degeneration; (ii) aneurysms or bulges; and (iii) arteriovenous malformations which act as short circuits. Hemorrhage and other incidents attributable to these pathologies or acute thrombogenesis leading to vessel constriction or blockage can led to stroke resulting in death or devastating disabilities. Diagnostic imaging as well as therapeutic image-guided procedures are used in the treatment of cerebrovascular diseases.

In the past, the treatment of choice for vascular disease was invasive surgery that inherently carries substantial risks. More recently, image-guided minimally invasive endovascular treatments are becoming increasingly preferred for medical treatment. Such endovascular treatments are primarily radiographically related procedures. As new procedures are developed involving smaller and smaller catheters and devices, great importance is placed on image quality. There is a growing requirement for high spatial resolution during endovascular interventions or treatment. For example, balloon expansion of a stent or attempts to mold the stent within the treated vessel depend upon images with adequate detail. Visualizing the spatial relationship between overlapping stents, where required, is difficult. Also, detecting the movement of stents during the placement process is challenging. With newer stents having smaller gauge wire and more complex design, it is becoming very difficult to see even the gross shape of the stent, let alone to determine the status of the individual segment or wires of such devices. As endovascular devices progress toward treatment of smaller vessels (i.e., within or beyond the Circle of Willis) there will be the additional concern about disturbing or blocking the origin or perforators. These perforators are micro in size and are often extremely important vessels for specific, key neurological functions, which if blocked can produce devastating effects in the patient. Perforators seen during invasive microsurgery typically cannot be visualized easily, if at all, during conventional image-guided endovascular procedures. For aneurysm treatment with detachable coils, the thin strands of overlapping coils are typically blurred together into a dense mass with standard equipment. Visualization of the detailed shape of the aneurysm and the location and spacing of coil loops could determine the success or failure of the treatment.

SUMMARY OF THE INVENTION

A method for visualizing a blood clot disposed within a body lumen comprising: binding a contrasting complex comprising a contrast material and a thrombolytic material to the blood clot; and visualizing the blood clot over a period time by a visualizing system. The method may be continuous or batch depending upon the application.

The body lumen is selected from the group consisting of: the cardiovascular system, the pulmonary system, the digestive system, the central nervous system, the reproductive system, and the excretory system. More particularly, the body lumen is selected from the group of: arteries, veins, capillaries and lymphatic vessels.

The contrast material is at least one selected from the group consisting of an ionic material, non-ionic material and mixtures thereof. Preferably, the contrast material comprises at least one heavy atom having an atomic weight of 30 or greater. The contrast material may comprise at least one metal. The contrast material is selected from the group consisting of: iodine, gadolinium, ultrasound contrast materials, and mixtures thereof. Moreover, the contrast material is selected from the group consisting of: metals, paramagnetic materials, high atomic number non-metal materials, radioisotopes, gases or gas precursors, chromatophores, fluorophores, electrical impedance materials, and any combinations thereof. Alternatively, the contrast material further comprises an endothelial binding substance. It is also optional that the contrast material is biodegradable.

The visualizing is over a period of time sufficient to permit the performance of image-guided invasive procedures selected from the group consisting of: diagnostic procedures, therapeutic procedures and any combinations thereof. The image-guided procedure is selected from the group consisting of: manipulation of wires, manipulation of balloons, manipulation of catheters, manipulation of stents, and diagnosis of gastrointestinal bleeding. Preferably, the visualizing system is selected from the group consisting of: radiography systems, nuclear medicine systems, ultrasound systems, magnetic resonance systems and any combinations thereof.

The thrombolytic material is at least one selected from the group consisting of: tissue plasminogen activator (tPA), tenecteplase form of TPAse, streptokinase, urokinase, retavase and any mixtures thereof. It is preferable that the contrast material binds to the thrombolytic material, wherein the bond between the contrast material and the thrombolytic material is at least one bond selected from the group consisting of: a molecular bond, ionic bonds, covalent bonds, metallic bonds, mixed bonds, polar and nonpolar covalent bonds and multiple bonds.

The contrasting complex preferably binds to the blood clot via a fibrin portion of the thrombolytic material, wherein the contrast material renders the blood clot radio opaque under x-ray imaging.

A contrasting complex for visualization of a blood clot disposed within a body lumen wherein the contrasting complex exhibits the following characteristics: (i) binds to the blood clot disposed within the body lumen for a period of time sufficient to perform invasive image-guided procedures selected from the group consisting of: diagnostic procedures, therapeutic procedures and any combinations thereof, wherein the body lumen is selected from the group consisting of: the cardiovascular system, the pulmonary system, the digestive system, the central nervous system, the reproductive system, and the excretory system; (ii) provides visibility of the blood clot by a visualizing system sufficient to perform the invasive image-guided procedures, wherein the visualizing system is selected from the group consisting of: radiography systems, nuclear medicine systems, ultrasound systems, magnetic resonance systems and any combinations thereof; and (iii) exits the body without causing either kidney toxicity, allergic reaction, or stimulation of atherogenesis.

A method for selectively binding a contrasting complex to a blood clot disposed within a body lumen comprising: administering an effective amount of a contrasting complex which exhibits the following characteristics: (i) binds or adheres to the blood clot disposed within the body lumen for a period of time sufficient to perform invasive image-guided procedures selected from the group consisting of: diagnostic procedures, therapeutic procedures and any combinations thereof, wherein the body lumen is selected from the group consisting of: the cardiovascular system, the pulmonary system, the digestive system, the central nervous system, the reproductive system, and the excretory system; (ii) provides visibility of the blood clot by a visualizing system sufficient to perform the invasive image-guided procedures, wherein the visualizing system is selected from the group consisting of: radiography systems, nuclear medicine systems, ultrasound systems, magnetic resonance systems and any combinations thereof; and (iii) exits the body without causing either kidney toxicity, allergic reaction, or stimulation of atherogenesis; and visualizing the blood clot by a visualizing system.

The period of time the contrasting complex binds to the blood clot is sufficient to permit the performance of image-guided invasive procedures selected from the group consisting of: diagnostic procedures, therapeutic procedures and any combinations thereof. The image-guided invasive procedure is selected from the group of: manipulation of wires, manipulation of balloons, manipulation of catheters, and manipulation of stents. The visualizing system is selected from the group consisting of: radiography systems, nuclear medicine systems, ultrasound systems, magnetic resonance systems and any combinations thereof.

A method for selectively binding a contrasting complex to a thrombus on a venerable plaque disposed within a body lumen comprising: (1) administering an effective amount of a contrasting complex which exhibits the following characteristics: (i) binds or adheres to the thrombus on the plaque disposed within the body lumen for a period of time sufficient to perform invasive image-guided procedures selected from the group consisting of: diagnostic procedures, therapeutic procedures and any combinations thereof, wherein the body lumen is selected from the group consisting of: the cardiovascular system, the pulmonary system, the digestive system, the central nervous system, the reproductive system, and the excretory system; (ii) provides visibility of the plaque by a visualizing system sufficient to perform the invasive image-guided procedures, wherein the visualizing system is selected from the group consisting of: radiography systems, nuclear medicine systems, ultrasound systems, magnetic resonance systems and any combinations thereof; and (iii) exits the body without causing either kidney toxicity, allergic reaction, or stimulation of atherogenesis; and (2) visualizing the plaque by a visualizing system.

Attachment of a clot paint to the thrombus on a vulnerable plaque, allows for early detection and assists in guiding stent placement or any another form of treatment, such as radiation or cryoablation or drug delivery.

DETAILED DESCRIPTION OF THE INVENTION

The present invention involves binding or adhering a blood clot or other clot disposed within a body lumen with a contrasting complex comprising a contrast material and a thrombolytic material, which adheres or binds to the blood clot for a period of time sufficient to permit visualization for performance invasive image-guided medical procedures, including diagnostic procedures, therapeutic procedures, and combined diagnostic and therapeutic procedures. Compositions for use in the present invention may be a contrast material or a material containing a contrast material in combination with another ingredient or several ingredients. Imaging may be affected by radiography, nuclear medicine, ultrasound, or magnetic resonance systems. Compositions of the invention are not toxic to the renal system or other system of the body, are not allergenic, and do not stimulate atherogenesis.

The present invention provides a method of imaging blood clots disposed in any of the mammalian or other animal lumens, including those of the circulatory system (i.e., arteries, veins, capillaries, and lymphatics), the pulmonary system (i.e., bronchi), the central nervous system (i.e., the spinal cord, brain, and nerves), the digestive system (small and large intestines, colon, liver, and bile ducts), the excretory system (kidneys, bladder and urological ducts), and the reproductive system (i.e., the uterus). Imaging may be done by any convenient system, including nuclear medicine imaging, preferably x-ray, magnetic resonance imaging (MRI). Cardiac angiography is a particularly preferred embodiment.

The term "contrast imaging agent" refers to any composition or material in any chemical form that is detectable in a diagnostic imaging procedure. Contrast materials may be organic or inorganic and are commonly metals or metal complexes or non-metals with high atomic weight (i.e., iodine). Iodinated contrast materials are a preferred embodiment. Contrast imaging material for use in the invention must efficaciously adhere, completely or in part, to a blood clot long enough to permit real time imaging sufficient to allow diagnosis of a medical condition and/or the performance an invasive medical procedure.

The active detection component of the contrast materials of the invention may be any material capable of detection either directly or indirectly in an in vivo diagnostic imaging procedure. Suitable materials are those which emit or may be caused to emit detectable radiation (i.e., by radioactive decay, fluorescence excitation, spin resonance excitation, etc.), materials which affect local electromagnetic fields (i.e., paramagnetic, superparamagnetic, ferrimagnetic or ferromagnetic species), materials which absorb or scatter radiation energy (i.e., chromophores; particles, including gas or liquid containing vesicles); heavy elements and compounds thereof, etc., and materials which generate a detectable substance (i.e., gas micro-bubble generators or the like).

A variety of materials detectable by diagnostic imaging may be employed. The preferred contrast material should be selected according to the desired imaging procedure. For example, with ultrasound imaging an echogenic material, or a material capable of generating an echogenic material will normally be selected. With X-ray imaging, the contrast material will generally be or contain a heavy atom, preferably having an atomic weight of about 30-38 or greater. With magnetic resonance imaging, the contrast material will either be a non-zero nuclear spin isotope or a material having unpaired electron spins and hence having paramagnetic, superparamagnetic, ferrimagnetic or ferromagnetic properties. For light imaging, the contrast material will be a light scatterer, either a colored or uncolored particle, a light absorber or a light emitter. With magnetometric imaging, the contrast material will have detectable magnetic properties. With electrical impedance imaging, the contrast material will affect electrical impedance. For scintigraphy, SPECT, PET or the like, the detected moiety will be a radionuclide.

Examples of contrast material materials are, for example, magnetic iron oxide particles, gas-containing vesicles, and chelated paramagnetic metals (i.e., Gd, Dy, Mn, Fe etc.). See, for example, U.S. Pat. Nos. 4,647,447; 4,863,715; 4,770,183; 5,228,446; 5,387,080; 6,303,101; 6,404,680; 5,447,711; 6,420,436; 6,310,243; 6,448,442; 6,149,891, and 6,051,207. These patents are incorporated herein in their entirety.

Particularly preferred as reporting or contrast materials are: chelated para magnetic metal ions, such as Gd, Dy, Fe, and Mn, especially when chelated by macrocyclic chelant groups (e.g. tetraazacyclododecane chelants, such as DOTA, DO3A, HP-DO3A and analogues thereof) or by linker chelant groups such as DTPA, DTPA-BMA, EDTA, DPDP, etc; metal radionuclides (i.e., such as those of Y, Tc, Sc, Ga, Cr, Sn, Cu, Tm, Ru, Re, Lu, Au, Pb and Ce); superparamagnetic iron oxide crystals; chromophores and fluorophores having absorption and/or emission maxima in the range between about 300 to 1400 nm, especially between about 600 nm to 1200 nm, most particularly between about 650 to 1000 nm; vesicles containing fluorinated gases (i.e., containing materials in the gas phase at 37° C. which are fluorine containing, chelated heavy metal cluster ions, e.g., W or Mo polyoxoanions or the sulphur or mixed oxygen/sulphur analogs); covalently bonded non-metal atoms which are either high atomic number (e.g., iodine) or are radioactive; iodinated compound containing vesicles; and the like.

In general, the active contrast, reporting, or detecting entity may be: (1) a chelatable metal or polyatomic metal-containing ion (i.e., TcO, etc), where the metal is a high atomic number metal (i.e., atomic number greater than about 30-37), a paramagnetic species (i.e., a transition metal or lanthanide), or a radioactive isotope; (2) a covalently bound non-metal species which is an unpaired electron site (i.e., an oxygen or carbon in a persistent free radical), a high atomic number non-metal, or a radioisotope; (3) a polyatomic cluster or crystal containing high atomic number atoms, displaying cooperative magnetic behavior (e.g., superparamagnetism, ferrimagnetisms or ferromagnetism) or containing radionuclides; (4) a gas or a gas precursor (i.e., a material or mixture of materials which is gaseous at 37° C.); (5) a chromophore (including fluorescent or phosphorescent material), e.g., an inorganic or organic structure, particularly a complexed metal ion or an organic group having an extensive delocalized electron system, or (6) a structure or group having electrical impedance varying characteristics.

Preferred contrast, reporting or detecting materials include chelated metal reporters including metal radionuclides, paramagnetic metal ions, fluorescent metal ions, heavy metal ions and cluster ions. Examples of referred metal radionuclides include $^{90}$Y, $^{99M}$Tc, 111In, $^{47}$Sc, $^{67}$Ga, $^{15}$Cr, $^{117m}$Sn, $^{67}$Cu, $^{167}$Tm, $^{97}$Ru, $^{188}$Re, $^{177}$Lu, $^{199}$Au, $^{203}$Pb and $^{141}$Ce. Preferred paramagnetic metal ions include ions of transition and lanthanide metals (i.e., metals having atomic numbers of 6-9, 21-29, 42, 43, 44, or 57-71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, more particularly of Mn, Cr, Fe, Gd and Dy, and especially Gd. Fluorescent metal ions for use in the invention include lanthanides, preferably La, Ce, Pr, Nd, Pm, Sm, Eu, Gd, Tb, Dy, Ho, Er, Tm, Yb, and Lu. Eu is especially preferred. Preferred heavy metal-containing materials may include atoms of Mo, Bi, Si, and W, and in particular may be polyatomic cluster ions (i.e., Bi compounds and W and Mo oxides).

The metal ions are desirably chelated by chelant groups in materials of the invention or on a particle (i.e., a vesicle or a porous or non-porous inorganic or organic solid), in particular linear, macrocyclic, terpyridine and $N_2$ S2 chelants, such as DTPA, DTPA-BMA, EDTA, D03A and TaT. Additional examples are disclosed in U.S. Pat. Nos. 5,367,080 and 5,364,613, which are incorporated herein in their entirety. A chelator or chelating agent is a compound containing donor atoms that can combine by coordinate bonding with a metal atom to form a cyclic structure called a chelation complex or chelate. A chelant or chelating group may comprise the residue of one or more of a wide variety of cheating agents known in the art that can complex a metal ion or a polyatomic ion.

A suitable chelating agent can be selected from polyphosphates, such as sodium tripolyphosphate and hexametaphosphoric acid; aminocarboxylic acids, such as ethylenediaminetetraacetic acid, N-(2-hydroxy)ethylenediaminetriacetic acid, nitrilotriacetic acid, N, N-di(2-hydroxyethyl)glycine, ethylene-bis(hydroxyphenylglycine) and diethylenetriamine pentacetic acid; 1,3-diketones, such as acetylacetone, trifluoroacetylacetone, and thenoyltrifluoroacetone; hydroxycarboxylic acids, such as tartaric acid, citric acid, gluconic acid, and 5-sulfosalicyclic acid; polyamines, such as ethylenediamine, diethylenetriamine, triethylenetetraamine, and triaminotriethylamine; aminoalcohols, such as triethanolamine and N-(2-hydroxyethyl)ethylenediamine; aromatic heterocyclic bases, such as 2,2'-diimidazole, picoline amine, dipicoline amine and 1,10-phenanthroline; phenols, such as salicylaldehyde, disulfopyrocatechol, and chromotropic acid; aminophenols, such as 8-hydroxyquinoline and oximesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, $(CH_3)_6$-[14]-4,11]-diene-$N_4$, and (2.2.2-cryptate); phosphonic acids, such as nitrilotrimethylene-phosphonic acid, ethylenediaminetetra(methylenephosphonic acid), and hydroxyethylidenediphosphonic acid, or combinations of two or more of the above agents. The residue of a suitable chelating agent preferably comprises a polycarboxylic acid group and preferred examples include: ethylenediamine-N,N,N',N'-tetraacetic acid (EDTA); N,N,N',N'',N''-diethylene-triamine-pentaacetic acid (DTPA); 1,4,7,10-tetraazacyclododecane-N, N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); and trans(1,2)-cyclohexanodiethylene-triamine-pentaacetic acid (CDTPA). Chelating agents may comprise proteins modified for the chelation of metals such as technetium and rhenium as described in U.S. Pat. No. 5,078,985, incorporated herein by reference.

Preferred chelating groups are 2-amiomethylpyridine, iminoacetic acid, iminodiacetic acid, ethylenediaminetetraacetic acid (EDTA), diethylenetriaminepentaacetic acid (DTPA), 1,4,7,10-tetraazacyclododecane-1,4,7,10-tetraacetic acid (DOTA), carbonyliminodiacetic acid, methyleneiminoacetic acid, methyleneiminodiacetic acid, ethylenethioethylene-iminoacetic acid, ethylenethioethyleneiminodiacetic acid, TMT, a terpyridinyl group, a chelating agent comprising a terpyridyl group and a carboxymethylamino group, or a salt of any of the foregoing acids. Especially preferred chelating groups are DTPA, DTPA-BMA, DPDP, TMT, DOTA and HPDO3A.

Methods for metallating chelating agents are within the level of skill in the art. Metals can be incorporated into a chelant moiety by direct incorporation, template synthesis and/or transmetallation. Direct incorporation is preferred. Metal ions can be easily complexed to chelating agent, for example, by merely exposing or mixing an aqueous solution of the chelating agent-containing moiety with a metal salt in an aqueous solution, preferably at a pH from about 4 to about 11. The salt can be any convenient salt, but preferably it is a water-soluble salt of the metal, such as a halogen salt, and more preferably such salts are selected so as not to interfere with the binding of the metal ion with the chelating agent. The chelating agent-containing moiety is preferably in aqueous solution at a pH from between about 5 to about 9, more preferably a pH of between about 6 to about 8. The chelating agent-containing moiety can be mixed with buffer salts, such as citrate, acetate, phosphate and borate to produce the optimum pH. Preferably, the buffer salts are selected so as not to interfere with the subsequent binding of the metal ion to the chelating agent. In diagnostic imaging, containing a metal radionuclide, a ratio of metal radionuclide ion to chelating agent that is effective should be used. In preferred embodiments, the mole ratio of metal ion per chelating agent is between about 1:1,000 to about 1:1.

Contrast materials or material for use in the invention may be non-metal atomic materials or organic chromophoric or fluorophoric materials. Preferred non-metal atomic reporters include radioisotopes such as $^{123}I$ and $^{131}I$ as well as non-zero nuclear spin atoms, such as $^{18}F$, and heavy atoms, such as I. The present invention preferably contemplates the use of radioisotopes of iodine. For example, if materials of the invention can be chemically substituted by iodine in a covalent bond forming reaction, such substituents can be labeled by methods well known in the art with a radioisotope of iodine. The iodine species can be used in diagnostic imaging applications. While, at the same time, a metal in a chelating agent can also be used in diagnostic imaging applications. As with the metal chelants discussed earlier, contrast materials may be or carried in or on a vesicle or other particulate material.

Preferred organic chromophoric and fluorophoric reporters include groups having an extensive delocalized electron system, i.e., cyanines, merocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes and the like. Examples of chromophores, which may be used, include xylene cyanole, fluorescein, dansyl, NBD, indocyanine green, DODCI, DTDCI, DOTCI and DDTCI. Groups which have maximum absorption between about 600 and 1000 nm are preferred so as to avoid interference with hemoglobin absorption.

Additional examples of organic chromophoric or fluorophoric agents include, but are not limited to, cyanine dyes, chalcogenopyrylomethine dyes, pyrilium dyes, thiapyrilium dyes, squarylium dyes, croconium dyes, azulenium dyes, merocyanine dyes, indoaniline dyes including Cu and Ni complexes, indanthrene pigments, trisphenoquinone dyes, azo dyes, non-benzenoid aromatic dyes, tetrazine radical dyes, anthraquinone dyes, naphthoquinone dyes, metallated azo dyes including those containing Ni, Co, Fe and Mn, phthalocyanine dyes, naphthalocyanine dyes, metal phthalocyanines, metal naphthalocyanines, bis(dithiolene) metal complexes, bis(benzenedithiolate) metal complexes, bis(S, O-dithiolene) metal complexes, and tris(a-diimine) metal complexes. Representative examples are found in U.S. Pat. No. 6,051,207, which is incorporated herein in its entirety.

Examples of visible dyes include, but are not limited to, fluorescein derivatives, rhodamine derivatives, coumarins, azo dyes, metalizable dyes, anthraquinone dyes, benzodifuranone dyes, polycyclic aromatic carbonyl dyes, indigoid dyes, polymethine dyes, azacarbocyanine dyes, hemicyanine dyes, barbituates, diazahemicyanine dyes, stryrl dyes, diaryl carbonium dyes, triaryl carbonium dyes, phthalocyanine dyes, quinophthalone dyes, triphenodioxazine dyes, formazan dyes, phenothiazine dyes, such as methylene blue, azure A, azure B, and azure C, oxazine dyes, thiazine dyes, naphtholactam dyes, diazahemicyanine dyes, azopyridone dyes, azobenzene dyes, mordant dyes, acid dyes, basic dyes, metallized and premetallized dyes, xanthene dyes, direct dyes, leuco dyes which can be oxidized to produce dyes with hues bathochromically shifted from those of the precursor leuco dyes, and any other visible dyes known in the art.

Particulate visualization agents include those where the particle comprises a matrix or shell which carries or contains the agent and those where the particle matrix is itself the agent. Examples of the first category include vesicles (i.e., micelles, liposomes, micro-balloons and micro-bubbles) containing a liquid, gas or solid phase which contains the contrast effective reporter (i.e., an echogenic gas or a precursor therefor), a chelated paramagnetic metal or radionuclide, or a water-soluble iodinated X-ray contrast material, porous particles loaded with the reporter, e.g., paramagnetic metal loaded molecular sieve particles; and solid particles (i.e., of an inert biotolerable polymer), onto which the agent is bound or coated (i.e., dye-loaded polymer particles).

Examples of the second category include, but are not limited to, light scattering organic or inorganic particles, magnetic particles (i.e., superparamagnetic, ferromagnetic or ferrimagnetic particles), and dye particles. Preferred particulate agents include superparamagnetic particles, echogenic vesicles, iodine-containing vesicles and dye-loaded polymer particles.

Non-peptidic endothelin receptors targeting vectors (such as, bosentan or BMS 182874) may be coupled directly or indirectly to a visualization agent, for example with covalently bound iodine radioisotopes, with metal chelates attached directly or via an organic linker group or coupled to a particulate agent (i.e., superparamagnetic crystals which are optionally coated), or a vesicle, (i.e., a gas containing or iodinated contrast material containing micelle, liposome or micro-balloon). The contrast materials of the invention may be conveniently administered to patients for imaging in amounts determined by those skilled in the art that are sufficient to yield desired contrast with the chosen imaging system.

The visualization agents of the present invention may be formulated with conventional pharmaceutical or veterinary aids, for example, emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. The visualization materials of the present invention may be in any conventional pharmaceutical administration form, such as tablets, capsules, powders, solutions, suspensions, dispersions, syrups, suppositories, etc. However, solutions, suspensions and dispersions in physiologically acceptable carrier media, for example water for injections, that adhere to lumen walls, will generally be preferred.

For imaging of some portions of the body the most preferred mode for administering contrast materials is parenteral, e.g., intravenous administration. Parenterally administrable forms, e.g., intravenous solutions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions, such as sodium chloride injection, Ringer's solution injection, dextrose injection, dextrose and sodium chloride injection, lactated Ringer's injection and other suitable solutions known in the art. The solutions may contain preservatives, antimicrobial agents, buffers and antioxidants conventionally used for parenteral solutions, excipients and other additives which are compatible with the chelates and which will not interfere with the manufacture, storage or use of products.

In one embodiment of the present invention, the contrast material may conveniently comprise a gas-containing or gas-generating material, preferably in suspension in an aqueous carrier material and conjugated to one or more materials of i.e., an endothelin antagonist. The gas may take the form of microbubbles stabilized by a monolayer of a film-forming surfactant, or stabilized by a matrix material other than a surfactant. The materials may be, for example, coupled to such surfactant or matrix and may be bioactive or non-bioactive. There may be different targeting specificities and in one preferred embodiment are such as to interact with their receptors but not to fixedly bind the gas-containing vesicles.

Particularly useful contrast materials are compounds or materials that are visible under x-ray (i.e., heavy metals, iodine, etc.). Regardless of the contrast material employed, the visualization of body lumens (i.e., arteries, veins, biliary ducts, gastrointestinal tract, lyphatics, bronchi, etc.), by traditional procedures has a time limitation perhaps best exemplified by iodinated contrast materials visualized by x-ray radiation. The iodinated contrast is injected into the target lumen and the lumen contents (i.e., blood) are displaced for a brief period (i.e., seconds) of time. X-ray imaging is preformed rapidly to record the displacement process and to image the target lumen such that the presence or absence of disease processes can be diagnosed. The contrast material is injected in bolus fashion and images must be obtained rapidly before the bolus has washed out. Repeated injections of contrast material are common. Each repetition of the imaging procedure adds cost, increases the probability of a medical complication, and adds radiation exposure to both the patient and the provider. The present invention provides for the use of material that is imagable contrast material and has the functional capability of adhering to the lumen wall or surface for a period of time. The period of time should be of sufficient duration so as to provide visualization for the performance of invasive diagnostic procedures, therapeutic procedures or combined diagnostic and therapeutic procedures. The adherence time may vary. Adherence of contrast material may from about 1 or a few seconds to about 1 hour or more. Adherence time is preferably from about 10 seconds to about 5 minutes, and more preferably from about 15 seconds to about 2 minutes, with an even more preferable time of at least 30 seconds. Thus, the material of the invention functions in effect as a clot paint providing extended time for visualization and thereafter being harmlessly removed from the body (i.e., biodegradation, excretion). The materials of the invention would adhere to the blood clot so as to permit direct real-time visualization of the clot structure. Such real-time visualization is useful for both diagnostics and therapeutics, and is particularly well suited for invasive image guided procedures where the clot paint may outline the thrombus on a plaque and aid as a targeting guide during sten placement, for example, arteries and veins being treated with wires, balloons, catheters, stents and the like, would be visible under fluoroscopy while the procedure is performed. Success of such procedures requires careful placement and device manipulation within small areas. Such procedures, i.e., stent placement, would be greatly facilitated by the materials and methods of the present invention. Stents could be accurately placed since the lumen or vascular paint-like materials of the invention would allow real-time visualization of the diseased target area during stent placement and/or angiography.

The materials of the invention may be used for a variety of medical diagnostic procedures involving lumen visualization, including, but not limited to, the diagnosis of circulatory or digestive system conditions. For example, the present invention may conveniently be used to diagnose gastrointestinal (GI) bleeding. Gastrointestinal bleeding may involve the vomiting of blood (hematemesis), the passage of black tarry stool material (melena), or the passage of blood from the rectum (hematochezia) which suggests a lower GI source of bleeding. While anoscopy, flexible sigmoidoscopy, colonoscopy, nuclear medicine and other diagnostic procedures and tests known in the art are useful, the diagnosis of GI bleeding is often difficult. For example, if the bleeding rate is greater than about 0.5 mL/minute and conventional contrast materials are used, angiography may show extravasation of contrast medium.

The use of clot-adhering contrast material would reduce radiation exposure to both the patient and operator during visualization procedures. Fluoroscopy generated images yield lower radiation doses to the patient and the operator than a digital angiographic acquisition. Iodine is a preferred contrast material. Its efficacy is well known in the art. However, iodinated contrast materials are nephrotoxic. Large volumes of contrast material are often needed during an interventional procedure to confirm results of the procedure (i.e., to confirm stent or balloon position). The present invention would significantly lower the load of iodinated contrast to the kidneys. Accordingly, the present invention would allow for angiographic interventions to be performed safely on patients with abnormal renal function who would not otherwise be a candidate for this procedure.

Yet another benefit or advantage of the present invention is that the contrast materials would predictably carry a decreased risk of allergic reaction to the contrast material since very little of the contrast material would come in contact with histiocytes in the lung vasculature. Also, the contrast materials would reduce costs by decreasing the quantity of expensive contrast material needed to complete a procedure.

The contrast materials of the invention may be an ionic or non-ionic contrast material (i.e., an iodine-containing moiety) or may be a suitable contrast material combined with a substance that binds or adheres to the blood clot, preferably an endothelial binding substance. Contrast materials known in the art may conveniently be screened in vitro or in vivo for the functional capability of temporary adherence to clots. Contrast materials of the invention are preferably liquid or gel, and more preferably are aqueous solutions, mixtures or suspensions. Other bioassay screening systems known in the art may be employed. In vivo screening of materials with laboratory animal may be used. Visualizing systems may be radiography systems, nuclear medicine systems, ultrasound systems, magnetic resonance systems or any combination of these systems.

A preferred method for visualizing a blood clot disposed within a body lumen comprises: binding a contrasting complex comprising a contrast material and a thrombolytic material to the blood clot; and visualizing the blood clot over a period time by a visualizing system. The method may be continuous or batch depending upon the application.

The body lumen is selected from the group consisting of: the cardiovascular system, the pulmonary system, the digestive system, the central nervous system, the reproductive system, and the excretory system. More particularly, the body lumen is selected from the group of: arteries, veins, capillaries and lymphatic vessels.

The visualizing is over a period of time sufficient to permit the performance of image-guided invasive procedures selected from the group consisting of: diagnostic procedures, therapeutic procedures and any combinations thereof. The image-guided procedure is selected from the group consisting of: manipulation of wires, manipulation of balloons, manipulation of catheters, manipulation of stents, and diagnosis of gastrointestinal bleeding. Preferably, the visualizing system is selected from the group consisting of: radiography systems, nuclear medicine systems, ultrasound systems, magnetic resonance systems and any combinations thereof.

The thrombolytic material is at least one selected from the group consisting of: tPA, tenecteplase (TN K) form of TPAse, streptokinase, urokinase, retavase and any mixtures thereof.

It is preferable that the contrast material binds to the thrombolytic material, wherein the bond between the contrast material and the thrombolytic material is at least one bond selected from the group consisting of: a molecular bond, ionic bonds, covalent bonds, etallic bonds, mixed bonds, polar and non-polar covalent bonds and multiple bonds.

The contrasting complex preferably binds to the blood clot via a fibrin portion of the thrombolytic material, wherein the contrast material renders the blood clot radio opaque under x-ray imaging.

A contrasting complex for visualization of a blood clot disposed within a body lumen wherein the contrasting complex exhibits the following characteristics: (i) binds to the blood clot disposed within the body lumen for a period of time sufficient to perform invasive image-guided procedures selected from the group consisting of: diagnostic procedures, therapeutic procedures and any combinations thereof, wherein the body lumen is selected from the group consisting of: the cardio-vascular system, the pulmonary system, the digestive system, the central nervous system, the reproductive system, and the excretory system; (ii) provides visibility of the blood clot by a visualizing system sufficient to perform the invasive image-guided procedures, wherein the visualizing system is selected from the group consisting of: radiography systems, nuclear medicine systems, ultrasound systems, magnetic resonance systems and any combinations thereof; and (iii) exits the body without causing either kidney toxicity, allergic reaction, or stimulation of atherogenesis.

A method for selectively binding a contrasting complex to a blood clot disposed within a body lumen comprising: administering an effective amount of a contrasting complex which exhibits the following characteristics: (i) binds or adheres to the blood clot disposed within the body lumen for a period of time sufficient to perform invasive image-guided procedures selected from the group consisting of: diagnostic procedures, therapeutic procedures and any combinations thereof, wherein the body lumen is selected from the group consisting of: the cardiovascular system, the pulmonary system, the digestive system, the central nervous system, the reproductive system, and the excretory system; (ii) provides visibility of the blood clot by a visualizing system sufficient to perform the invasive image-guided procedures, wherein the visualizing system is selected from the group consisting of: radiography systems, nuclear medicine systems, ultrasound systems, magnetic resonance systems and any combinations thereof; and (iii) exits the body without causing either kidney toxicity, allergic reaction, or stimulation of atherogenesis; and visualizing the blood clot by a visualizing system.

The period of time the contrasting complex binds to the blood clot is sufficient to permit the performance of image-guided invasive procedures selected from the group consisting of: diagnostic procedures, therapeutic procedures and any combinations thereof. The image-guided invasive procedure is selected from the group of: manipulation of wires, manipulation of balloons, manipulation of catheters, and manipulation of stents. The visualizing system is selected from the group consisting of: radiography systems, nuclear medicine systems, ultrasound systems, magnetic resonance systems and any combinations thereof.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the following claims.

What is claimed is:

1. A method for selectively binding a contrasting complex to a blood clot or a thrombus on a plaque disposed within a body lumen comprising:

administering an effective amount of a contrasting complex comprising a contrast material and a thrombolytic material, wherein said contrasting complex: (i) binds or adheres to said blood clot or said thrombus disposed within said body lumen via a fibrin portion of said thrombolytic material for a period of time sufficient to perform an invasive image-guided procedure, wherein said body lumen is selected from the group consisting of: the cardio-vascular system, the pulmonary system, the digestive system, the central nervous system, the reproductive system, and the excretory system; (ii) provides real-time visualization of said blood clot or said thrombus by a visualizing system during said invasive image-guided procedure, wherein said visualizing system is selected from the group consisting of: radiography systems, nuclear medicine systems, ultrasound systems, magnetic resonance systems and any combinations thereof; and (iii) exits said body without causing either kidney toxicity or stimulation of atherogenesis; and visualizing said blood clot or said thrombus by said visualizing system, wherein said contrast material renders radio-opaque said blood clot or said thrombus under x-ray imaging, and wherein said thrombolytic material is selected from the group consisting of: tissue plasminogen activator (tPA) tenecteplase form of TPAse, streptokinase, urokinase, retavase, and any mixtures thereof.

2. The method of claim 1, wherein said image-guided invasive procedure is selected from the group of: manipulation of wires, manipulation of balloons, manipulation of catheters, and manipulation of stents.

3. The method of claim 1, wherein said contrast material is selected from the group consisting of: an ionic material, non-ionic material and mixtures thereof.

4. The method of claim 1, wherein said contrast material comprises at least one heavy atom having an atomic weight of 30 or greater.

5. The method of claim 1, wherein said contrast material comprises at least one metal.

6. The method of claim 1, wherein said contrast material is selected from the group consisting of: iodine, gadolinium, ultrasound contrast materials, and mixtures thereof.

7. The method of claim 1, wherein said contrast material is selected from the group consisting of: metals, paramagnetic materials, high atomic number non-metal materials, radioisotopes, gases or gas precursors, chromatophores, fluorophores, electrical impedance materials, and any combinations thereof.

8. The method according to claim 1, wherein said contrast material binds to said thrombolytic material.

9. The method according to claim 8, wherein the bond between said contrast material and said thrombolytic material is selected from the group consisting of: a molecular bond, an ionic bond, covalent bond, metallic bond, mixed bonds, polar and nonpolar covalent bonds, and multiple bonds.

* * * * *